United States Patent
Iuliano (10) Patent No.: US 7,116,415 B2
(45) Date of Patent: Oct. 3, 2006

(54) METHOD AND APPARATUS FOR DETECTING CHEMICAL AND BIOLOGICAL WEAPON COMPONENTS USING RAMAN SPECTRUM

(75) Inventor: Michael J. Iuliano, Point Pleasant Beach, NJ (US)

(73) Assignee: In Technology Holding LLC, Toms River, NJ (US)

( * ) Notice: Subject to any disclaimer, the term of this patent is extended or adjusted under 35 U.S.C. 154(b) by 72 days.

(21) Appl. No.: 10/872,032

(22) Filed: Jun. 18, 2004

(65) Prior Publication Data

US 2005/0280814 A1    Dec. 22, 2005

(51) Int. Cl.
  *G01J 3/44* (2006.01)
  *G01N 21/65* (2006.01)

(52) U.S. Cl. ................................... 356/301

(58) Field of Classification Search ............... 356/301, 356/317, 318
See application file for complete search history.

(56) References Cited

U.S. PATENT DOCUMENTS

| 6,914,668 | B1 * | 7/2005 | Brestel et al. | 356/310 |
| 2004/0051867 | A1 * | 3/2004 | Brestel et al. | 356/301 |

* cited by examiner

*Primary Examiner*—F. L. Evans
(74) *Attorney, Agent, or Firm*—Gottlieb, Rackman & Reisman, P.C.

(57) ABSTRACT

An analyzing apparatus and method generates a laser beam at a target. The Raman scattered photons from the target are collected and used to generate a Raman spectrum indicative of the composition of materials associated with the target, such as components of chemical or biological weapons. In one embodiment, a laser beam is generated with two streams of photons, the photons of one beam being entangled with the photons of the other beam. One stream is then directed at the target and only the other beam is analyzed to obtain said Raman spectrum. Alternatively, the scattered photons from the second beam are also analyzed and the results are correlated for greater efficiency and accuracy.

17 Claims, 8 Drawing Sheets

METHOD AND APPARATUS FOR DETECTING CHEMICAL AND BIOLOGICAL WEAPON COMPONENTS USING RAMAN SPECTRUM

RELATED APPLICATIONS: METHOD AND APPARATUS FOR PERFORMING IN-VIVO BLOOD ANALYSIS USING RAMAN SPECTRUM

Ser. No. 10/872,033 filed on Jun. 18, 2004.

BACKGROUND OF THE INVENTION

1. Field of Invention

The present invention describes a system and method for detecting chemical and or biological weapon components. The preferred embodiment is accomplished by creating two separate beams, consisting of monochromatic, coherent, polarized, quantum state entangled, exclusive or nearly exclusive co-incident photons. Then directing one beam, the probe beam, at a person or object, and analyzing the resulting conventional Raman backscatter spectrum while simultaneously directing the other beam, the detector beam, at a remote detector in order to analyze the changes in the quantum state characteristics of the entangled photons.

2. Background of the Invention

Various methodologies exist for detector technologies, for both chemical warfare and biological warfare agents. Currently, detector technology for both chemical warfare and biological warfare agents is strongest in terms of "detect to respond" or "detect to react" rather than "detect to warn." Most only respond when the threat is directly present. Alerting civilians, first responders or troops to the immediate danger of agent exposure is often the only goal of a detector. More sophisticated or additional instrumentation further refines the nature and concentration of the danger. The efficacy of these instruments to detect and alert of imminent danger play an important part in security issues in a multitude of potential forums. One of the most challenging aspect for chemical and biological agent identification is quickly extracting the agent of interest from the other chemicals in the environment. In this aspect, however, these detector methods are often ineffective, have long standing delays in data analysis, constantly need replacement, are easily damaged or destroyed by exposure to analytes they are supposed to detect. The currently deployed detection systems require multiple platforms for detecting various biological and or chemical agents. This is complicated, expensive undertaking.

Of course, the process of screening of individuals and their belongings for potentially dangerous components is a laborious and uncertain process. Boredom and complacency at checkpoints from constant repetitive searching, along with the constant pressure to keep the line moving, can lead to breakdowns in security. For this reason, technologies capable of scanning large volumes of people from a distance have been investigated with great interest.

The accurate and specific determination for existence of chemical or biological compounds on a human subject or their belongings, without performing an invasive procedure, has several advantages. These advantages include deterring the creation, transportation or use of potentially life threatening devices, higher levels of security to individuals in large public areas, such as, airports, train stations, sports arenas and government and military facilities, and faster, safer, less invasive screening procedures. These advantages encourage usage in areas that were previously unable to be monitored, such as train and bus terminals, and increased vigilance at facilities already being monitored.

Current methodologies for screening detection are primitive at best. They are really nothing more than moving a complex laboratory out into the "field". Representative examples of biological weapon detection techniques include:

Culturing or literally growing a colony of microbes on a nutrient containing surface (Petri-dish) and observing it with the eye or through a microscope. This is still the "gold standard" for identification of microbiological species.

Immunoassay-based detectors mimic the human body's natural immune system. Genetic-Based Detectors are another method, DNA or RNA isolated from a sample is exposed to nucleic acid sequences, or oligonucleotides, which correspond to a suspected biological agent.

Point Detectors directly examine potential biological agent-containing samples. Examples are:

Aerosol Particle Sizers (APS) in which particles are drawn through an orifice into a steady high-speed air flow.

Mass Spectrometry is another method to characterize potential Biological or chemical agents of interest by fragmenting them into progressively smaller charged pieces ending with constituent amino acid or protein pieces.

Surface Acoustical Wave Sensors are based on piezoelectric materials (those that produce an electrical current when subjected to pressure or mechanical stress) coated with antibodies or complimentary nucleic acid sequences.

Colorimetric Sensors are based on a visible color change and are, consider the fastest, cheapest, lightest and easiest type of detector to use.

Electrochemical or chemiresistor detectors, use the way electrical current changes in response to an interaction with a CW agent.

Ion mobility spectrometry (IMS) or plasma chromatography relies on small differences in the velocity of ions along a cylindrical tube, a "drift tube", across which a constant electric field is applied.

Mass Spectrometry combined with gas chromatography is the most sensitive and most reliable technique.

Flame photometric detection (FPD), is another method where a sample is ignited in a (very small) hydrogen flame.

Photoionization detector (PID) systems use ultraviolet (UV) light to ionize (remove the most loosely held electrons) from a vapor or gas.

Isotopic Neutron Spectroscopy is a non-destructive method for the evaluation of an agent in a sealed container.

Portable Isotopic Neutron Spectroscopy System (PINS) is employed in the field to differentiate traditional munitions from those containing CW agents.

Acoustic Resonance Spectroscopy (ARS) and Swept Frequency Acoustic Interferometry (SFAI). The two related techniques, rely on the fundamental difference in the speed of sound through a solid versus a liquid.

In contrast to point detectors there is another method called Remote or Standoff Detection. The primary goal with this methodology is to create a platform which allows for both monitoring and surveillance of potential biological and chemical agents at a distance. This is similar to Cloud Recognition for weather reporting which use of Doppler radar. LIDAR is another common tool used for cloud detection and recognition and is based on the same physical principles as radar, except instead of bouncing longer wavelength radio waves off a target, higher energy light waves are used. This technology has been adapted by the U.S. Army's Long-Range Biological Standoff Detection System (LR- BSDS) which uses LIDAR-based technology to detect aerosol clouds from long distances. The Short-Range Biological Standoff Detection System (SR-BSDS) combines infrared (IR) LIDAR with ultraviolet light reflectance (UV).

Another technique unlike many discussed above is Raman Backscattering or Raman Spectroscopy. This technique can be used for scanning both objects and individuals. The underlying science involves the way in which light scatters off any surface. That is to say, when light of any wavelength impinges on a surface (or molecule), most of the scattered photons are elastically (or Rayleigh) scattered. That means that they leave with the same frequency (or wavelength) as the incident radiation. In contrast to this there is a small fraction of the scattered light (less than one in a thousand incident photons) that is inelastically (or Raman) scattered at frequencies that differ from the incident frequency by a value determined by the molecular vibrations of the sample. Raman scattering creates a discrete molecular spectrum at frequencies corresponding to the incident frequency plus or minus the molecular vibrational frequency. A Raman spectrum is thus a plot of the intensity of scattered light as a function of frequency (or wavelength). By convention, Raman spectra are shown on an orthogonal graph with the wave numbers (reciprocal centimeters) along the horizontal axis and the abscissa representing intensity or energy.

Raman spectra have long been used to determine the structure of inorganic and biological molecules, including the composition of complex multicomponent samples. Raman spectroscopy is considered to have many advantages as an analytical technique. Most strikingly, it provides vibrational spectra that act as a molecular fingerprint containing, unique, highly reproducible, detailed features, thereby providing the possibility of highly selective determinations.

In comparing Raman scattering verses other forms of analysis, the Raman approach is advantageous for several reasons:

(1) Solid, liquid and gas states can be analyzed
(2) Aqueous solutions present no special problems
(3) No special pre-scanning preparation of the sample is necessary
(4) The low frequency region is easily obtained.
(5) The device can be made inexpensive lightweight and portable
(6) Scanning can be completely non invasive and clandestine
(7) Scanning distance can be varied from centimeters to kilometers.

Several previous inventors have recognized the potential for using Raman scattering as a non-invasive (NI) sensor for scanning individuals. U.S. Pat. No. 6,574,501 discusses assessing blood brain barrier dynamics or measuring selected substances or toxins in a subject by analyzing Raman spectrum signals of selected regions in aqueous fluid of the eye. U.S. Pat. No. 5,553,616 discloses the use of Raman scattering with excitation in the near infrared (780 nm) and an artificial neural network for measuring blood glucose. WO 92/10131 discusses the application of stimulated Raman spectroscopy for detecting the presence of glucose. U.S. Pat. No. 6,070,093, describes a noninvasive glucose sensor that combines Raman measurements with complementary non-invasive techniques in order to enhance the sensitivity and selectivity of the measurement.

Other previous inventors have recognized the potential for using Raman scattering for non-invasively scanning of objects. U.S. Pat. No. 6,608,677 discloses the use of a Mini-lidar sensor for the remote stand-off sensing of chemical/biological substances and method for sensing same. U.S. Pat. No. 6,593,582 discloses a Portable digital lidar system, which in part could use raman backscattering. U.S. Pat. No. 4,802,761 dicusses Optical-fiber raman spectroscopy used for remote in-situ environmental analysis.

Still other previous inventors have recognized the potential for using entangled photons for scanning of objects. U.S. Pat. No. 5,796,477 discloses an entangled-photon microscope, for WF fluorescence microscopy.

A major challenge for all of the Raman techniques to date has been to collect spectral information with sufficiently high signal-to-noise ratios to discriminate weak analyte signals from the underlying background noise.

Existing non-invasive in vivo Raman measurements are hindered by a number of factors, including notoriously low quantum efficiency. In other words, very few inelastic scattering events occur in comparison to the number of elastic scattering events. Conventionally, in non-resonance Raman spectroscopy in order to double the efficiency of Raman scattering it is necessary to square the photon density. Unfortunately this can damage the sample. Therefore it is necessary to perform scans at either long integration times or high power densities to achieve acceptable signal-to-noise (S/N) ratios.

Other forms of Raman scattering like, resonance and surface enhancement or the combination of both can significantly improve the sensitivity and selectivity of Raman measurements. However, these enhancements are not generally applicable to all analytes or to all samples, especially in living, breathing, moving targets. Furthermore relating band intensities to analyte concentrations under such circumstances requires careful calibration procedures, which is obviously not helpful in high volume screening applications.

SUMMARY OF THE INVENTION

Briefly, the present invention pertains to a system and method in which a laser beam, is generated and used to scan along individuals and or their belongings to detect for potential elements or compounds that can be used as weapons, or to create weapons.

The novelty of this invention is to use two phenomena in quantum mechanics called non-locality and superpositon. Non locality is a counter intuitive characteristic where seperate photons can share a single quantum state. (This is kind of analogous to two cars 50 miles apart running off the same carburetor). Superposition, on the other hand, is the sharing of a single temporal and spatial state. (This is kind of analogous to two cars using the same parking spot at the same time).

In essence this invention is a raman spectrometer that has been modified to significantly amplify raman backscatter and to detect the change in the quantum state characteristics of the raman backscatter. The implication of this is that objects at a distance do NOT need to be near a detector. This allows for the free movement of both objects and individuals while keeping the power density of the scanning beam very low. Another aspect of this invention is to use diffraction to tune the frequency of the scanning beam so as to create both surface and penetrating scanning.

The overall technique is accomplished by processing a laser beam through spontaneous parametric downconversion geometry to create two separate quantum entangled beams whose photons are in superposition.

In one embodiment of the invention, the laser source uses SPDC or other known phenomena to generate pairs of entangled photons.

In one embodiment, the entangled photons are sent along an optical path to cause them to propagate in superposition.

In one embodiment, one of the entangled superposition beams is directed in a sweeping probe beam toward the target individual and their belongings and the resulting conventional Raman back scatter is intercepted, collected and analyzed.

In one embodiment, both of the entangled superposition beams are directed in a sweeping probe beam toward people and their belongings and the resulting conventional Raman back scatter is intercepted, collected and analyzed.

In one embodiment, one of the entangled superposition beams is directed in a sweeping probe beam toward people and their belongings while the other beam, the detector beam, is sent to a quantum state characteristic detector. As the probe beam interacts with the target, a quantum state change occurs in the probe beam, at the level of the sample, as a function of Raman backscatter. This change in quantum state will be "transferred to" or "shared by" the remote detector beam. Polarization detection is a common technique used in Raman spectroscopy. By carefully creating the down converted beams to have their polarization entangled, the geometry of the system can be set to read, for example, fractional depolarization per specific frequency. In this way the unique finger print vibrational modes of an analyte can be determined. This makes it possible to obtain chemical or biological constituents without actually collecting and analyzing the Raman back scattered photons.

In another embodiment, both the conventional raman backscatter from the probe beam and the quantum state changes from the detector beam are analyzed and the results are correlated for increased redundancy and accuracy.

In another embodiment, other types of quantum state characteristics are entangled in the probe and detector beams.

In one embodiment of the invention, various articles of clothing or exposed body parts (hands, arms, feet or legs) of the subject are located and the beam is directed by a tracking system to scan them for a time period sufficient to collect the necessary Raman back scatter.

In another embodiment, the tracking system is used to direct the beam across the surface of personal belongings, such as brief cases and purses, and filtering is used to detect only Raman back scatter corresponding to any particular material.

In either case, the tracking system insures the beam never enters vital areas of the subject, such as the face or eyes. Moreover, the intensity of the laser beam is kept at a low level known to be safe.

DETAILED DESCRIPTION OF THE INVENTION

The present invention describes a system and method for performing chemical and biological weapon detection. This is accomplished by directing a probe beam (such as a monochromatic, coherent, polarized, quantum state entangled, exclusive or nearly exclusive co-incident photon beam) at a subject or materials in that subject possession (including articles of clothing, wallets, jewelry, brief cases, etc.) and analyzing the resulting conventional Raman backscatter spectrum and the changes in the quantum state characteristics of the entangled photons.

It is well known, in Raman spectroscopy, that in order to improve the quantum efficiency, it is necessary to increase the photon density. But the relatively high power densities used in this technique can cause sample damage or destruction, which is unacceptable, especially when individuals or their possessions are the samples. The high power density may also induce black body interference, due to heating by the laser, which may further obscure the Raman spectrum.

An intuitive solution would be to attenuate the laser power to the point where the power density is below the sample damage or destruction level. The major drawback with this approach is that the "normal" or intrinsic amount of Raman scattering has very low efficiency and therefore produces a weak signal in the first place. Attenuating the signal further can cause the loss of the Raman spectrum in the background noise because its intensity is directly related to the total number of photons impinging on the sample. Therefore, any reduction in laser power to the sample must be counterbalanced by increasing the acquisition time. This leads to acquisition times that can reach hours per sample versus seconds or minutes. Another problem is that the probe beam creates natural phosphorescence of many chemicals and biomocules which interferes and masks Raman backscattering signal and makes it more difficult to distinguish the resultant Raman spectrum. Thus there is a need for an apparatus and method of making quick, safe, accurate, and reliable in situ analysis using Raman phenomena.

The present invention provides several solutions to this problem that can be utilized concurrently or independently of each other. Scanning moving people can be thought of as scanning either a gas or liquid samples. Its just the location of the substances of interest are located on the "particles floating" in the sample. More particularly, according to the present invention, the probe beam is not directed at a particular section of an individual for an extended time period but, instead, it is substantially continuously sweeping across an area, thereby reducing the time during which any particular part of an individual is exposed thereto. This also helps minimize confounding fluorescence. (Since raman backscatter is instantaneous and fluorescence has a time delay the scanner/detector has already moved on before any fluorescence can occur). The photons scattered by the sample are collected and analyzed to determine various characteristics of chemical and biological components therein.

Other major advantages of the invention are that, the sample data can be scanned and obtained in situ. This means multiple individuals can be evaluated simultaneously. Another major advantage of raman is that since the sample being scanned does not need preparation for analysis continuous operation of the device is possible which translates directly to real time detection and analysis and improved checkpoint flow patterns.

Figure 1A:
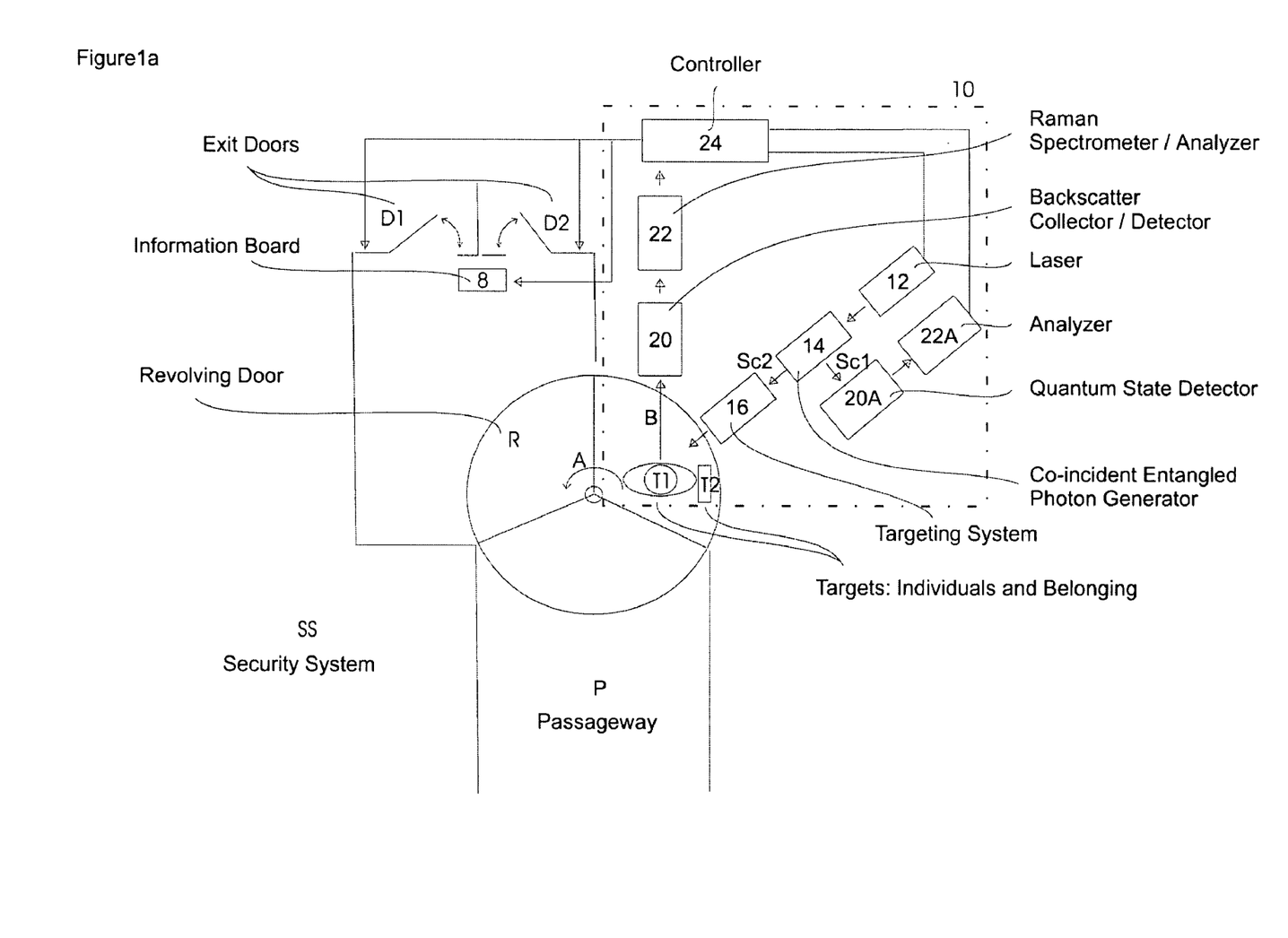
FIG. 1a shows a plan view of a security installation using a detector constructed in accordance with this invention.
Figure 1B:
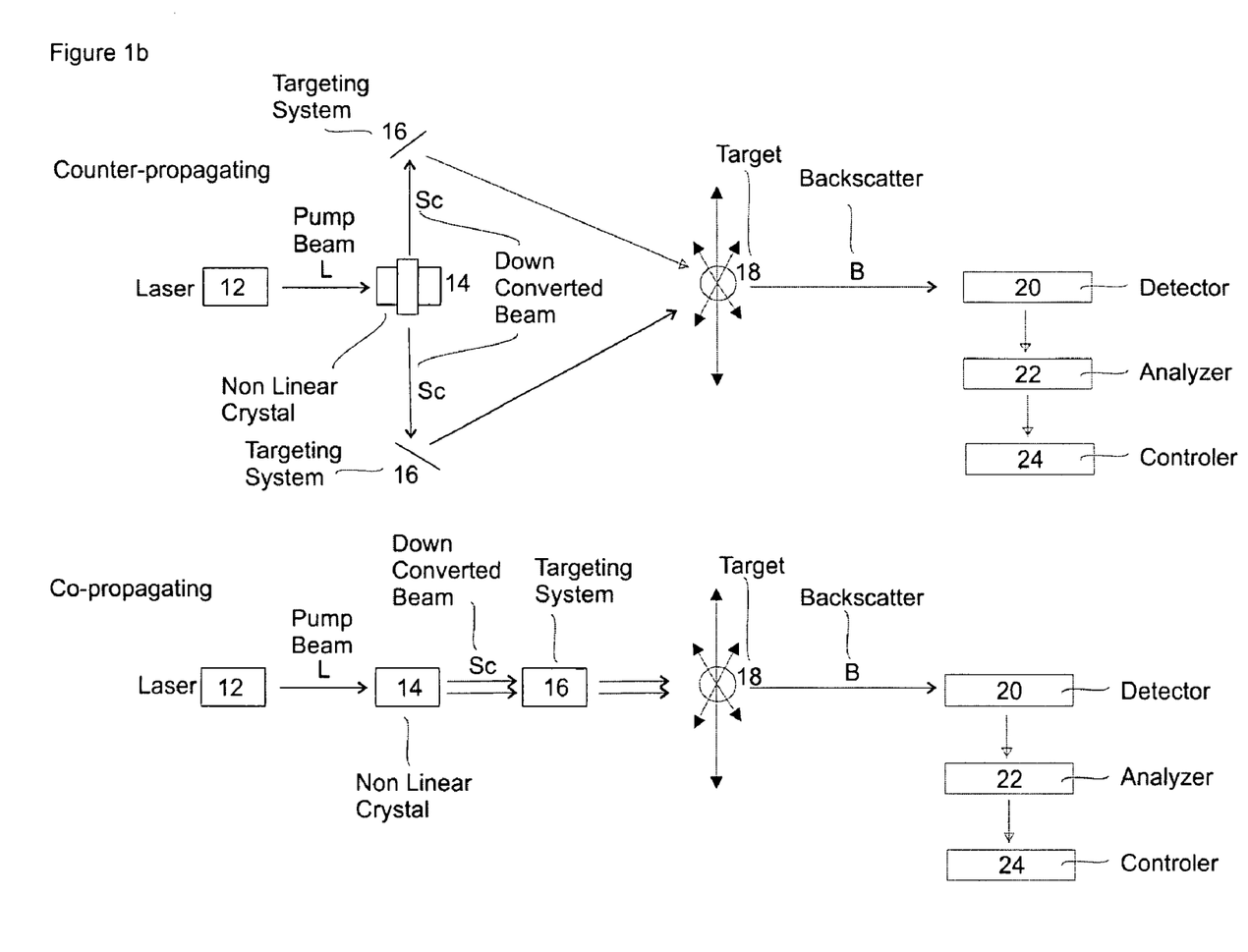
FIG. 1b shows a block diagram of the apparatus used for detecting weapons or their components in accordance with this invention.

FIGS. 1a and 1b show one embodiment of the invention. FIG. 1a shows a security station SS including a passageway P, two exit doors D1 and D2, a revolving door R. People passing through the station SS first enter through passageway P leading to the revolving door R. As the door R revolves in the direction A, each person passes the detector 10, and then goes to either door D1 or D2, in accordance with directions on sign S. The sign S and doors D1, D2 are controlled by the detector 10. Optionally, additional signs Sa and other output devices are provided at other locations through which detector provides messages and alarms to various security personnel, for example, indicating whether each target tested has passed or failed.

The detector 10 is adapted to identify certain substances that may be found in minute quantities on each person, or on objects carried by the person. This is accomplished by directing a laser beam at target T1 and/or T2, T1 being either a fixed or a moving target on the clothes of a person and T2 being a fixed or moving target on an object carried by the person. The positions of targets T1 and T2 are determined manually (for example, by an attendant directing the laser beam at particular spots) or automatically (using, for example, a pattern recognition algorithm that recognizes certain predetermined elements or positions either on a person's body or an object carried by the body). As indicated above, the laser beam can be directed either at a relatively small spot on the target, or alternatively, the beam may be used in either a predetermined pattern or a random pattern across the surface of the target T1, T2.

Referring to FIG. 1b, the detector 10 includes a laser beam generator 12, an SPDC converter 14, an aiming mechanism 16, a Raman backscatter detector 20, an analyzer 22 and a controller 24. Generally speaking, the device 10 operates as follows. The generator 12 generates a laser probe beam L having a predetermined population of photons. The beam is down converted by SPDC converter 14 or other similar means into a second laser beam Sc that includes entangled photon pairs, as discussed in more details below.

The second beam Sc is directed by aiming mechanism 16 onto a target 18. This aiming may be performed either manually (for example, by a security attendant) or automatically. Moreover, as discussed above, the beam may be directed at a single spot on the target, or may scan the target in a pattern.

As is well known in the art, the laser beam induces a Raman backscatter of photons B that have properties indicative of various particles and substances imbedded into, or disposed on the target T1/T2. This backscatter is sensed by a detector 20. The detector then generates a corresponding Raman spectrum. This spectrum is fed to an analyzer 22 that generates an output signal. This output signal is indicative of what substances were found or not found by the analyzer 22. The output signal is fed to the controller 24 that generates, in response, a control and/or display signal. The control signal may be operating the doors D1, D2 and the display signal generates a display on sign S and on other screens. The controller may also generates various reports.

Figure 1C:
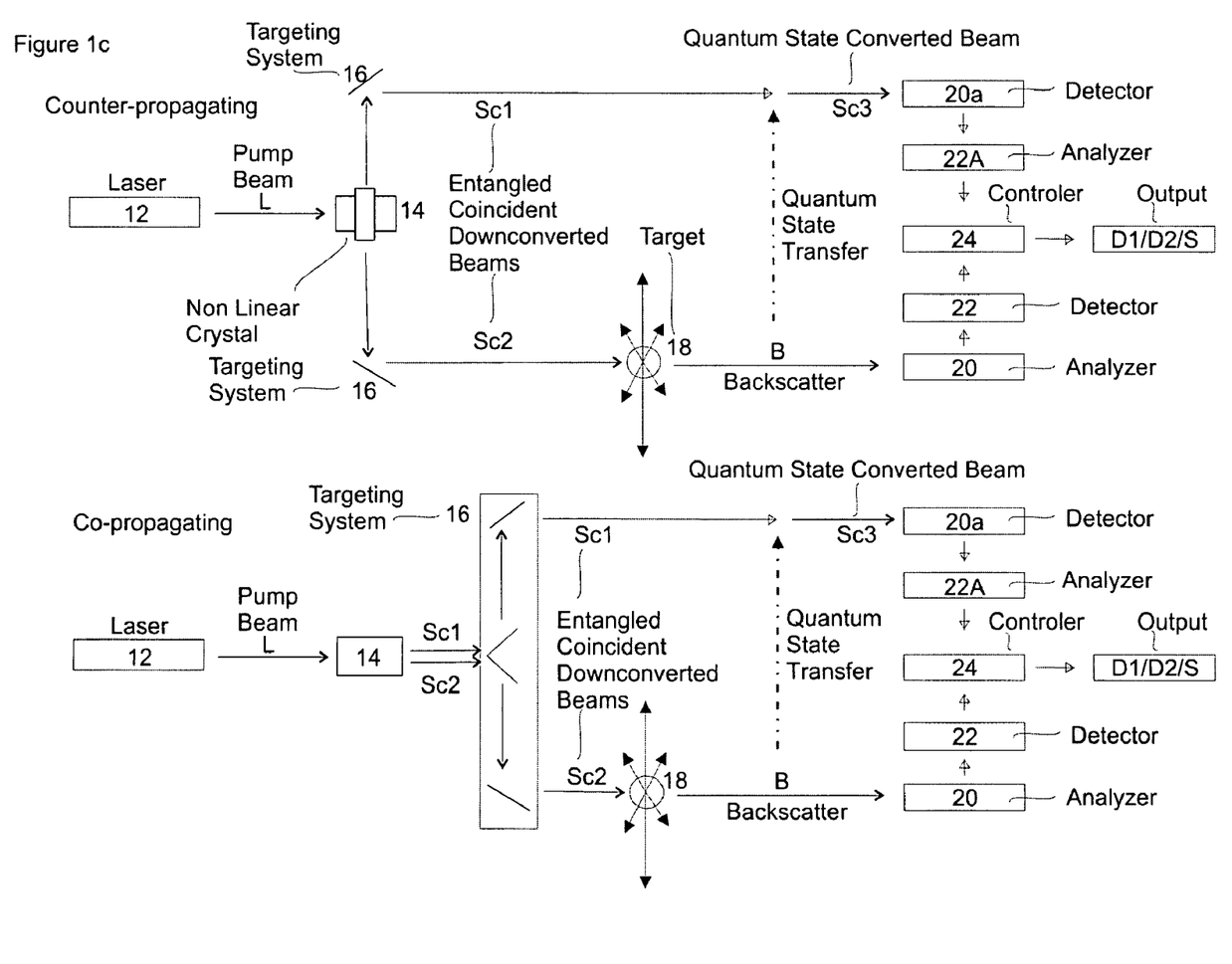
FIG. 1C shows an alternate block diagram of the apparatus used for detecting weapons or their components in accordance with this invention.

The alternate embodiment shown in FIG. 1c takes advantage of the entangled photon pairs generated by converter 14. In this embodiment, the converter SPDC 14 generates two photon beams Sc1 and Sc2. The beam Sc2 is handled in the same manner as the beam Sc in FIG. 1b. In accordance with the laws of quantum mechanics governing SPDC and entanglement, beam Sc1 will be converted to beam Sc3 as Sc2 interacts with the target and is converted to beam B. This happens because Sc1 and Sc2 are entangled and share the same quantum characteristics and therefor contain the same quantum information. In this embodiment, beam Sc3 is used to instaneously observe or detect the quantum state changes which occur the in the transformation of Sc2 to B. The respective quantum state change characteristics from detectors 20,20a are fed to respective analyzers 22, 22A the results from the two analyzers 22, 22A are combined, or the controller 24 compares the oututs of the analyzers and determines which one is to be used. Simultaneously the conventional Raman backscatter detector 20 generates a Raman spectrum and feeds this to the Raman spectral analyzer 22. Alternatively, the detector 20 and analyzer 22 are omitted and only the output from detector 20A is used by the analyzer 22a.

Raman backscatter is normally difficult to detect because of the high signal-to-noise ratio of the environment from which it gets collected. The present invention provides several methods of solving this problem. The first method pertains to the frequency of the excitation used to create Raman back-scatter. More specifically, the probe beam generated by the laser generator 12 has a wavelength selected preferably in the NIR region of about 700–1400 nanometers. This wavelength range insures that interference with fluorescence is reduced. Further reducing confounding fluorescence can be achieved by continuously moving the probe beam across the sample while pulsing the beam. Since Raman backscatter and fluorescence (the decay of long-lived electronic excitations) have different time delays, the extended shouldering of the fluorescence can be effectively ignored from each new sample zone. Other frequencies from radio to gamma could be used depending on the distance to the target medium through which the probe beam must pass and penetration depth of the target desired. It should be also noted that protective eyewear could be worn while people pass through the scanning area in order to facilitate high power scans.

The second method is to increase the number of photons in the probe laser beam that reach the sample simultaneously while reducing the photons that do not add significantly to the production of the Raman back scatter. Unlike conventional Raman, which uses massive photon volume to achieve a "random co-incidence" of photons in its signal production, the embodiment of this device is to produce a beam of photons that already share the same temporal and quantum state. That is, a portion of the highly energetic photons of the initial pump beam laser undergoes Spontaneous Parametric Down Conversion (SPDC). SPDC is when a higher energy photon passes through a non-linear crystal and is transformed into two photons of lower energy. If the geometry of the system is set correctly, all or nearly all the newly created lower energy photons of the probe beam are quantum entangled and overlapped or co-incident in space and time. This in effect changes the doubling of Raman emission efficiency from the square of the density of the photon beam to a linear function. This is because almost all the photons which produce the Raman effect at low efficiency have been replaced with co-incident photons which have a much better probability of producing Raman back scatter. This also has the beneficial effect of decreasing the overall energy introduced to the tissue.

Figure 2:
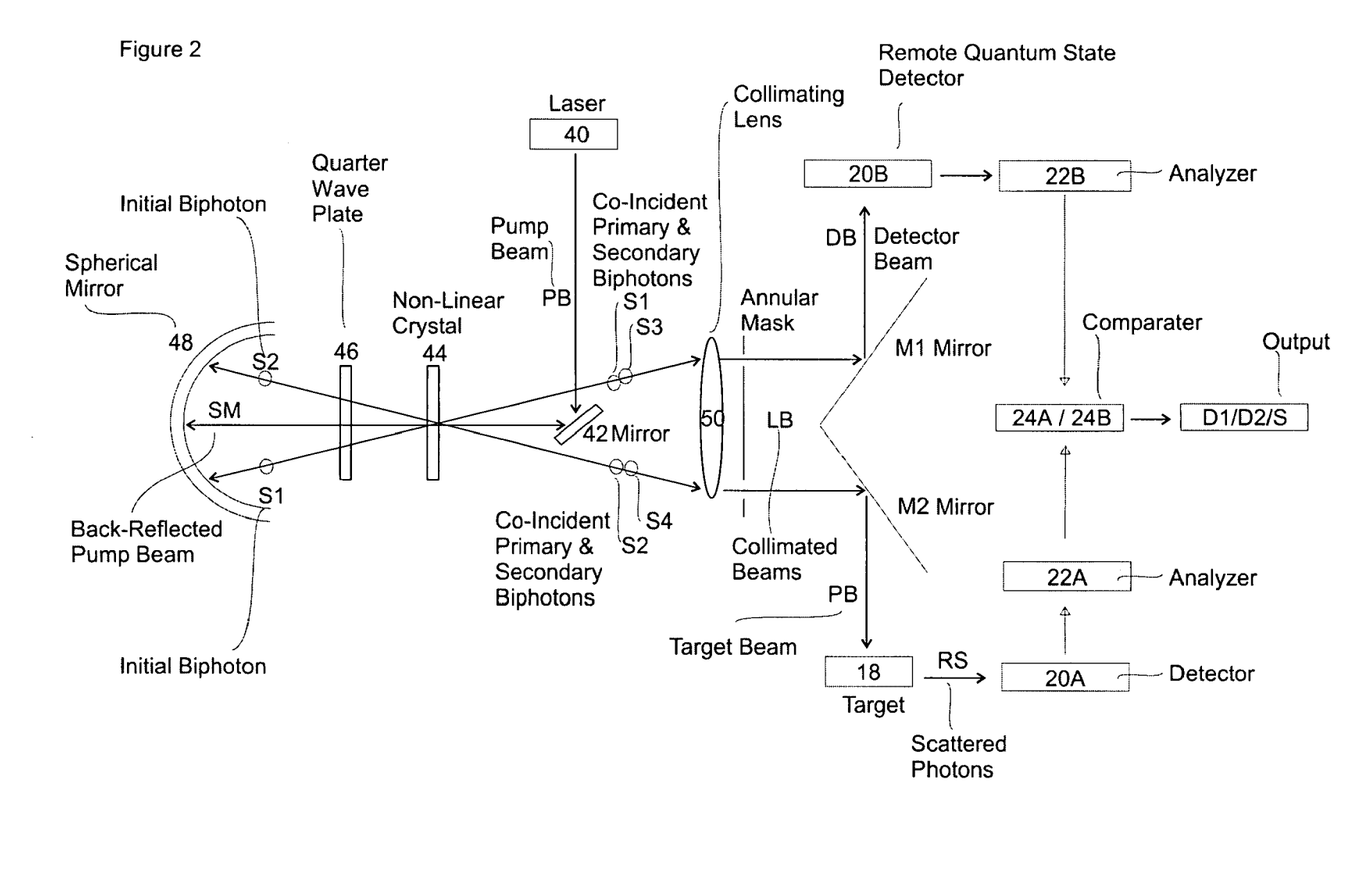
FIG. 2 shows a block diagram of a laser pump beam undergoing SPDC to generate the probe beam used in the apparatus of FIGS. 1a and 1c.
Figure 3:
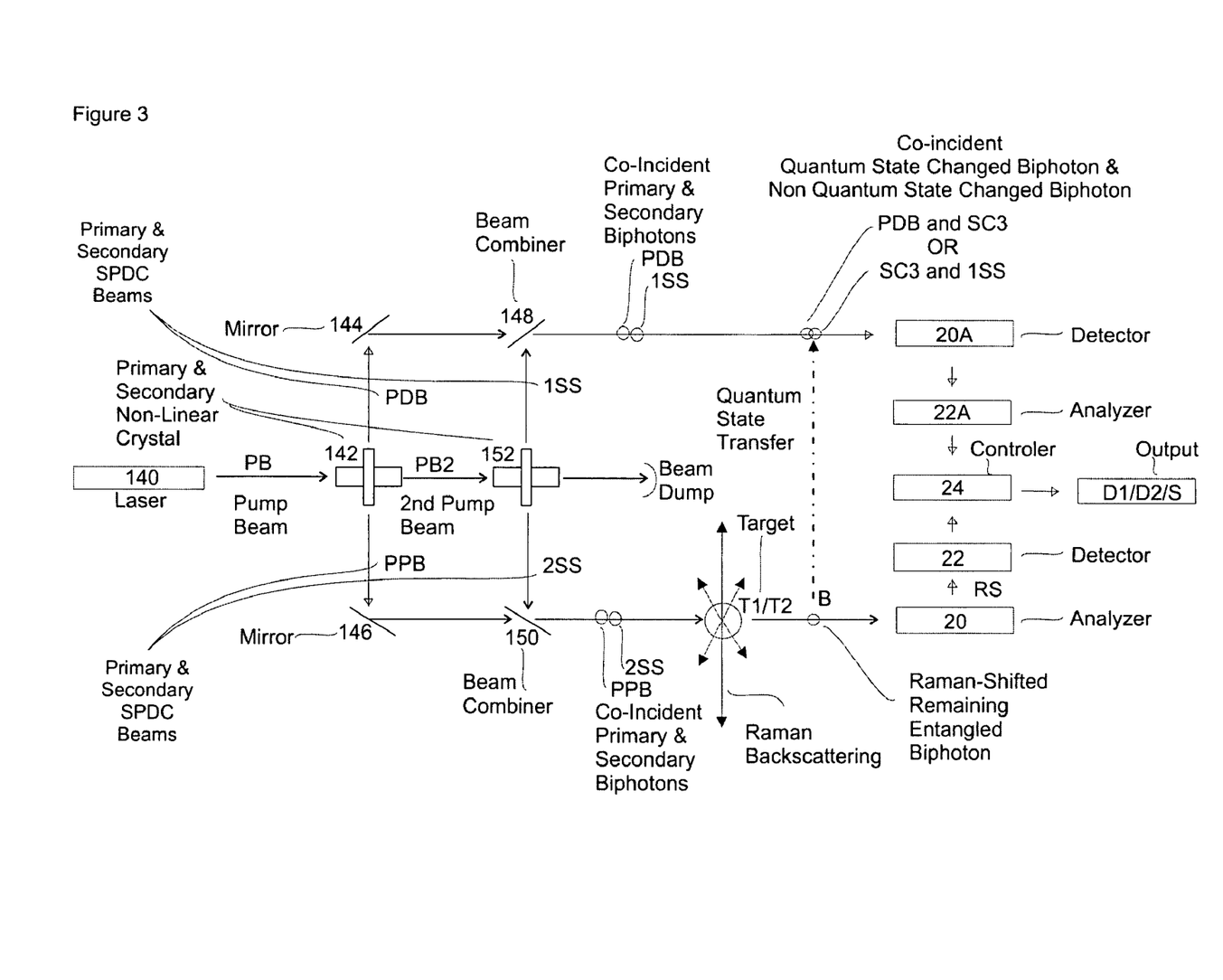
FIG. 3 shows a block diagram of an alternate method in which the laser pump beam undergoes SPDC to generate the probe beam used in the apparatus of FIGS. 1a, 1c.

The third method is to utilize the fact that when highly energetic photons undergo SPDC they split into a pair of lower energy photons that share entangled quantum states, commonly polarization and/or frequency. By carefully setting the geometry of the SPDC photon production, two separate beams of co-incident quantum state entangled photons can be created, each containing one half of the original quantum state entangled photon pair sitting in superposition with other similar photons. One stream, the probe beam, is used to scan across an individual or objects, and the resulting Raman scattering is determined from the characteristics of the conventionally backscattered photons. The second beam is sent on to a remote detector. Due to the fact that the second photon stream is quantum state entangled with the primary probe beam, it will undergoes the same quantum state change as its entangled pair in the probe beam. Since the remote detector beam never interacts with the sample is not affected by noise, thereby making the change in photon characteristics much easier to extract. Two types of apparatus demonstrating these principles are shown in FIGS. 2 and 3, FIG. 2 shows a somewhat preferred of many configurations creating a probe beam formed of quantum state entangled co-incident photons through SPDC (See U.S. Pat. No. 6,424,665 and article G Giorgi et al; A High Brightness Parametric Source of Entangled Photon States). It includes a pump laser 40 generating a pump beam PM. The pump beam is directed to a mirror 42 that directs it through a type I non-linear crystal 44 made of BBO and having a 32.6 degree orientation, a quarter-wave plate 46, a spherical mirror 48 having a radius equal to its distance to the crystal 44, and a collimating lens 50.

There are several well known lasers that can be used for the pump 40. Some of these are listed below.

Quantum Stack Laser
Gas Laser
Dye Tunable Laser
Semi Conductor Laser
Diode Laser
Quantum Dot laser The Quantum stack laser or a multi-frequency quantum dot laser that is particularly suitable as the pump beam generator because it can be set to produce beams at several discrete frequencies simultaneously. This becomes important as an additional method to improve the signal to noise ratio. As mentioned above Raman spectra is a reflection of the vibrational state of an atom or molecule plus or minus the frequency of the incident light. In a complex multicomponent sample, background fluorescence and spectral signals of components of non-interest can overlap the spectral signal of the component of interest. In order to further reduce these confounding signals it is advantageous to use probe beams of several frequencies that are carefully chosen to produce spectra of the analyte where different confounding signals may present but not initial confounding signals. It should be noted that multiple frequencies are especially helpful with extracting Raman from over lapping fluorescence. This is because that although the fluorescence spectrum is shifted from the laser frequency, the fluorescence shift depends on the laser frequency whereas the Raman shift does not. This to will aid in further delineating Raman from fluorescence signals. In this way, after multivariate analysis is applied to each frequency spectra the results can be compared. This in turn will lead to a higher confidence level.

The generator 12 operates as follows. Generally speaking, the probe beam generator 18 makes use of a single-arm interferometer to create probe beam LB comprising monochromatic coherent polarized exclusively or nearly exclusive co-incident photon pairs. The primary beam is reflected by mirror 42 through crystal 44 and plate 46 unto mirror 48. Mirror 48 returns this beam as a secondary beam SM through the plate 46, crystal 44 and mirror 42 to the pump 40. Crystal 44 causes a portion of both the primary and the secondary beams to undergo spontaneous parametric down-conversion as they pass therethrough. The geometry of SPDC generates a pair of coincident conically shaped beams linearly polarized. The beams are formed by the quantum superposition of the states created by spontaneous parametric down conversion of photons from the primary and secondary beams. All (SPDC) photon pairs are emitted at a predetermined wavelength, in this case of 727.6 nm. Two beams of photons S1 and S2 resulting from the pumped beam PM hit the mirror 48. These beams S1, S2 are returned to lens 50 and have arc shape. In addition, the secondary beam SM causes the generation of two more beams of photons S3 and S4. These latter beams are coincident in time and space with the beams S1, S2 respectively and are also coincident on the lens 50 as shown. In one embodiment of the invention, the lens 50 coverts the photon beams S1, S2, S3, S4 into a single colimated ring shaped laser beam LB. This beam LB is more effective then standard beams because it constitutes two sets of coincident photons S1, S3 and S2, S4 generated as discussed above. The beam LB is then directed at the target T1/T2 and the resulting Raman back scatter is gathered by collector 20 and fed to a detector 22.

However, preferably, the device also takes advantage of the fact that the beams resulting from lens 50 contain entangled photon pairs. The importance of entangled pairs of photons is that the state of one photon of a pair can be determined from the state of the other, even if the photon pairs are separated by great distances. Thus, a detector system is constructed in which the entangled photon pairs are separated, and then one photon (from a probe beam) is sent toward the sample and the second photon (from a detector beam) is sent towards a remote detector. The probe beam photons that strike the sample undergo Raman back scattering and the change in their quantum state is transferred to the corresponding entangled photons in the remote detector beam. In conventional Raman backscatter photons scatter in all directions but only the photons that bounce directly back to the detector can be collected analyzed. In contrast, quantum entanglement detection allows one to determine the status of all the photons of the probe beam independently of the direction in which they scatter, or even the need of collecting the scattered photons. Thus, while in a conventional Raman back scatter device, only about 25% of the photons are collected and analyzed, in a Raman back scatter detector using entangled photons, all 100% of the photons are available for quantum state analysis. Moreover, if the backscatter photons are collected in the conventional manner described above, and their quantum state is also analyzed, the two results may be combined. This means that the upwards of 125% of the actual quantum state changes are available to generate a molecular structure. In addition the conventional Raman spectrum would also be available.

Referring back to FIG. 2, instead of collimating the beams, S1, S2, S3 and S4, two mirrors M1 and M2 are used to direct these beams in different directions. More particularly, the photon beams S1, S3 form the detector beams that are directed toward a detector such as the Raman spectrum generator and Entangled Quantum Characteristic Detector 24A similar to generator 24 in FIG. 1. The photon beams S2, S4 form the probe beam that are directed at the target T1/T2 and their status can be determined from the detector beam since the photons S2, S4 are entangled respectively with the photons S1, S3. Alternatively, the photons back scattered from the sample 12 can be gathered by collector 22 and directed at Raman spectrum generator and Conventional Quantum Characteristic Detector 24. The results from two generators 24, 24A can be collated or combined to determine the Raman spectrum with even more certainty. In yet another embodiment of the invention, the mirror 48 is replaced by lens 50. In this embodiment, only primary entangled photon beams S1, S2 are generated. Since the photons of these beams are still entangled, they can still be used to form respective probe and detector beams. However, since the secondary beam SB is omitted the Raman effect will be greatly reduced because no superposition photons exist in the probe beam.

Referring now to FIG. 3, an alternate embodiment of a laser beam generator 118 incorporating these principles includes a pump 140 that generates a primary pump beam PB for an optical element 142. Element 142 may be, for example, a type I (idenically polarized signal and idler photons) SPDC crystal in a single-mode nonlinear waveguide pumped by a beam perpendicular to the wave guide. Element 142 generates a primary detector beam PDB, a primary probe beam PPB, and an attenuated secondary pump beam PB2. Mirrors 144 and 146 direct beams PDB and PPB towards mirrors 148, 150 respectively. Pump beam PB2 is directed at a second optical element 152. Element 152 generates from pump beam PB2 two secondary streams 1SS and 2SS consisting of a respective photon of the entangled photon pairs. Mirrors 148, 150 are structured so that they allow the transmission of the respective primary beams and reflect the secondary streams 1SS and 2SS. Each of these beams combine with the respective coincident beams from mirrors 144, 146. Thus the beams from mirrors 148, 150 have similar structures to the two beams from lens 50 in FIG. 2. The beam from mirror 148 could be the detector beam directed at Raman spectrum generator and Entangled Quantum Characteristic Detector 24A, while the beam from the mirror 150 could be the probe beam directed at target T1/T2. The result from generator 24A can be used in its own. Alternatively, the photons scattered from the target T1/T2 are collected and used by generator 24 to obtain another Raman spectrum and Conventional Quantum Characteristics. The results from generators 24 and 24A can then be combined as discussed above.

Figure 4:
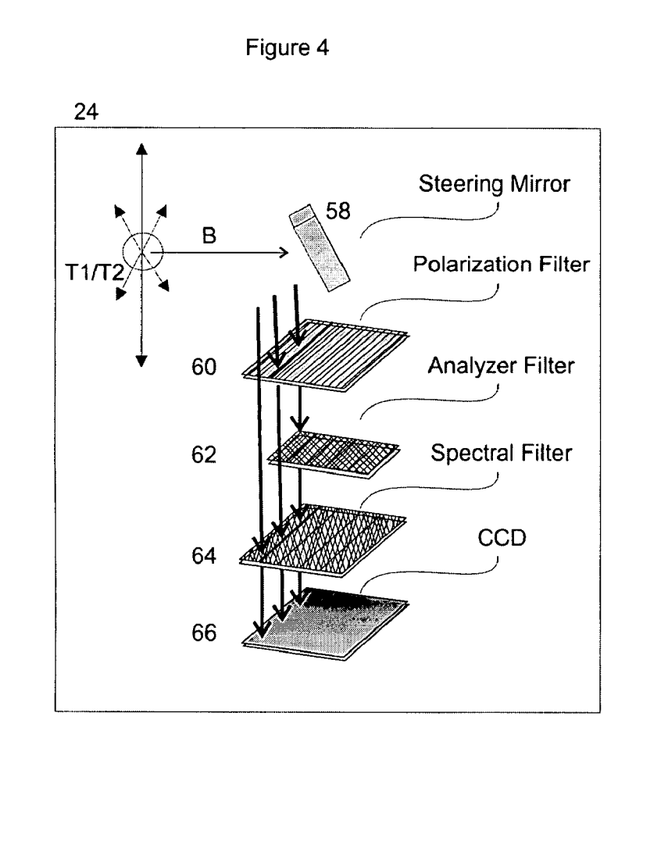
FIG. 4 shows details of the Raman spectrum generator of the apparatus of FIGS. 1a, 1b, 1c.
Figure 4A:
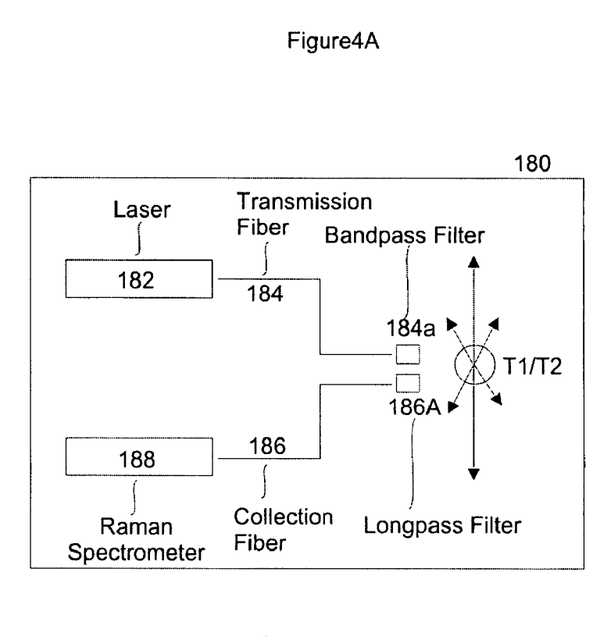
FIG. 4a shows a prior art Raman spectrum generator that can be modified to implement the generator of FIG. 4.

FIG. 4 shows details a Raman spectrum generator and Entangled Quantum Characteristic Detector 24 receiving the beam from the collectors of FIG. 2 or 3. This beam from the collector 22 is transmitted to spectrum analyzer 24 that consists of a steering mirror 58 and several superimposed layers that may have a square, rectangular, oval or other geometric shape. These superimposed layers are set up to allow the beam to be swept along their length so as to pass through different combinations of layers. The steering mirror 58 directs the beam first towards a holographic notch filter 64 and through to a photon detector (CCD) 66. This yields Raman shift peaks. The beam is then swept further along the so it passes through a polarization filter 60 and on through a holographic notch filter 64 and through to a photon detector (CCD) 66. This yields information of only portions of the beam that are polarized in a direction A. Next, the beam is then swept further along the so it passes through again a polarization filter 60 and on through to a secondary polarization filter, the analyzer filter 62, a holographic notch filter 64 and through to a photon detector (CCD) 66. This process is repeated across an array detector until all polarization positions have been determined for every frequency of interest. When a complete set of polarization components per frequency has been determined the sample depolarization ratio has been achieved. This can be converted to an analyte profile and its concentration.

The spectrum analyzer 24 can be either a high or a low-resolution analyzer. Deciding which spectrometer is appropriate will depend on the specific application.

High-resolution spectrometers could be easily applied to this invention, because they are exquisite at single spectrum analysis. This platform would be wonderfully adept at screening for the presence of multiple biological and chemical agents.

In contrast low resolution Raman spectrometers are well suited for repetitive concentration analysis of systems containing of known analytes. Then warning when of a change in the system occurs.

For the sake of brevity, since a both high and low resolutions setups for this invention are similar, an example of a low resolution set is discussed below. Though a high resolution spectrometer could obviously be substituted by any one skilled in the art.

Figure 5:
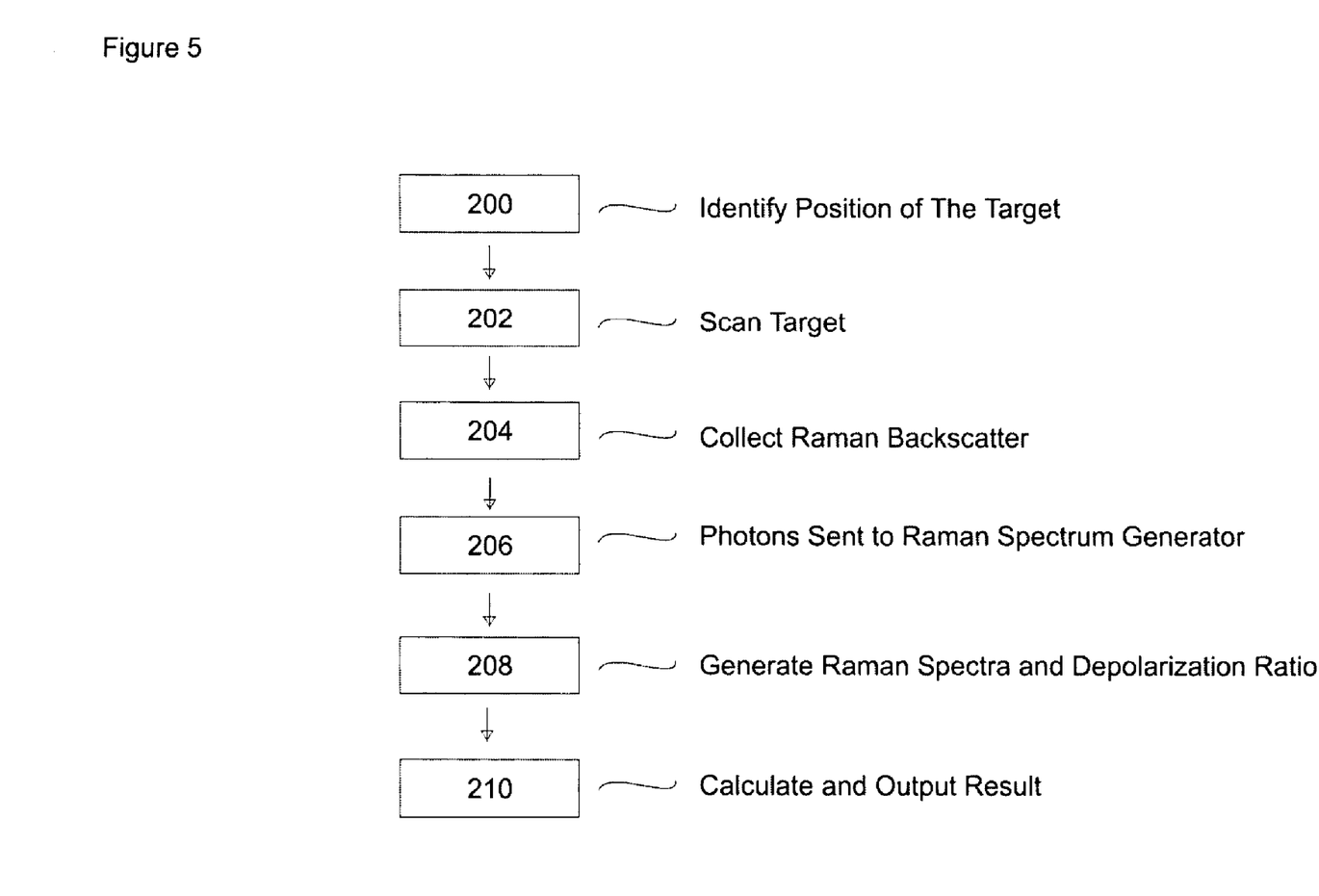
FIG. 5 shows a flow chart describing the operation of the apparatus of FIG. 1.

The basic components of a Low Resolution Raman Spectrometer (LRRS) instrument 180 are shown in the schematic illustration of FIG. 5. The instruments includes a multimode laser diode 182 and a bifurcate fiber optic bundle consisting of a delivery arm 184 and a collecting arm 186. The output of the laser 182 is injected into the delivery arm 184 which then delivers the laser beam to the sample (in this case, the target). The tip of the delivery arm 184 is provided with a bandpass filter 184A that removes silica-Raman frequencies and fiber fluorescence from the excitation beam. The collection fiber 186 is tipped with a long-pass filter 186A for Rayleigh and anti-Stokes Raman scattered light rejection. This type of LRRS instrument is available as the Raman Systems R-2001 manufactured by Boston Advanced Technologies (Marlboro, Mass., USA) and Ocean Optics (Dunedin, Fla., USA). It uses a 785 nm multimode solid-state diode laser provided by Power Technologies. (Little Rock, Ak., USA), adjusted to deliver 400 mW to the sample, and an Ocean Optics S-2000 miniature spectrometer as the monochrometer 188. The diode laser 182 provides a 2 nm wide excitation line. In the present invention, this laser is replaced with one that will produce in the UV wavelength which is then downconverted to the near-infrared range. The S-2000 uses an uncooled 2048-element linear silicon CCD array to measure spectra from 0 to 2700 $cm^{-1}$. The estimated sensitivity of the array elements is 86 photons per count and their well depth at 600 nm is 350 000 photons. The S-2000 uses a single dispersion grating with a line density of 1200 lines/mm. With the 50 micrometer slit selected, the S-2000 has a spectral resolution of approximately 20/cm. The resulting overall resolution of the R-2000 is approximately 30 cm.

The LRRS instrument is modified in the present invention in that it uses a different sample illumination system and in the detector array. While the above LRRS uses conventional laser light to cause Raman back scattering, the invention use the laser source generating monochromatic, coherent, polarized, quantum state entangled, exclusively or nearly exclusive co-incident photon pairs as described above. This allows for significant attenuation of the probe beam while still achieving a strong spectral signal at or below the MPE for ocular tissue. The detector also differs in that it will consist of an array of detectors laid out to detect not only spectrum but also quantum state information. Of course, the other modification is that the ends of the fiber bundles are directed by the tracking mechanism to scan the target as discussed above.

Figure 4B:
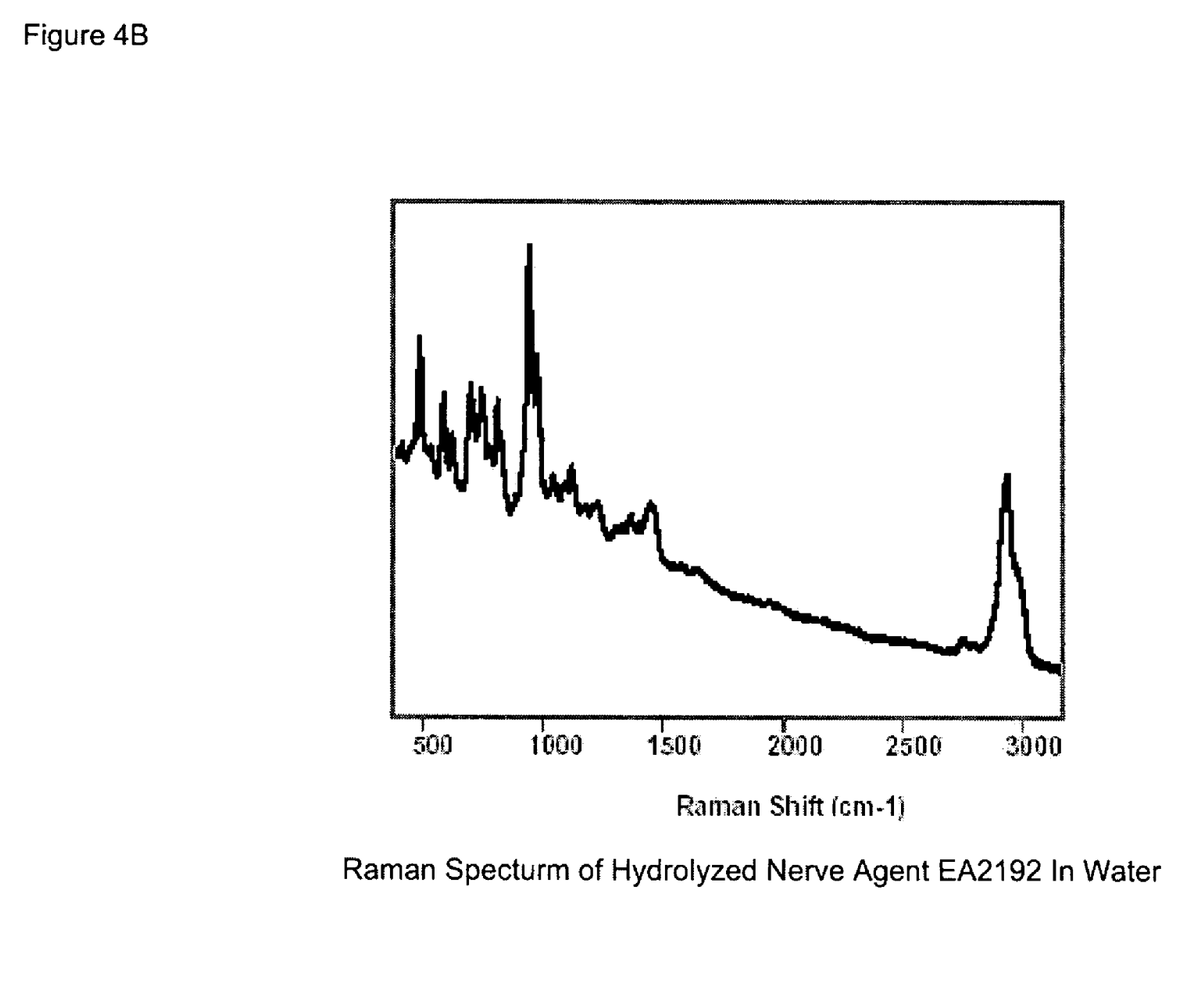
FIG. 4b shows a typical Raman spectrum for a hydrolyzed product of VX nerve agent.

A typical Raman spectrum (Surface enhance technique) characteristic of A hydrolized biproduct of VX nerve agent is shown in FIG. 4b. The amplitude of the signal is indicative of the concentration.

Alternatively, the concentration is obtained from the depolarization ratio, also available from the Quantum state characteristic generator.

Raman backscatter is by nature partially polarized, even for molecules in a gas or liquid state, where the individual molecules are randomly oriented. Raman backscatter from totally symmetric vibrations will be strongly polarized parallel to the plane of polarization of the incident light. The scattered intensity from non-totally symmetric vibrations is ¾ as strong in the plane perpendicular to the plane of polarization of the incident light as in the plane parallel to it. By determining the number of symmetrical and non-symmetrical modes present per frequency of a sample spectrum, chemical structures within a sample can be elucidated.

The apparatus for performing the detection of chemical and biological weapons may be structured and arranged to perform in several modes of operation. For example, the whole apparatus can be set up in an airport, a train station, sports complex, a hospital, a school or even a city street. Then the chemical and biological weapon detection results can be made available as soon as the computations are completed. Alternatively, the apparatus may be deployed in an Emergency Response Vehicle such as an Ambulance, Fire Truck or Helicopter in order to evaluate the on site biological or chemical hazard. The actual process could also be deployed in such a manner to allow only the scanning and detection components to be on site while the other data processing components may be in a remote, centralized location. The raw data collected, could be sent to this remote location and then analyzed. The results are then sent back, real time, to the scanning site by whatever method was appropriate (voice, fax, email, other electronic means or hard copy).

FIG. 5 shows a block diagram of the process used by the apparatus of FIG. 1. In step 200 the position of target T1/T2 is identified. In step 202 the target is scanned with the laser beam from generator 18. For the embodiment of FIG. 1, the laser beam is directed at the target whose positions have been determined in step 200. Alternatively, the target is scanned randomly or in a predetermined pattern and photons are directed at various parts distributed across the target. The tracking mechanism insures that during this process photons are not directed into the face or eye of a person to insure that he or she does not suffer any injury.

In step 204 the Raman scatter resultant from the photons is collected.

In step 206 the Raman scatter is provided to the Raman spectrum generator 24. In step 208 the desired Raman spectrum including frequency, amplitude, polarization ratio or other similar parameters are obtained by the Raman spectrum generator 24.

In step 208 these parameters of the Raman spectrum are analyzed by the analyzer and then the results are presented in any desired form.

The embodiments of FIGS. 2 and 3 are operated in the same manner. The apparatus described above can be used to apply Raman back scatter to detect various chemical components used as weapons or to create weapons including chemical components:

The apparatus described above can be used to apply Raman back scatter to detect various biological components used as weapons or to create weapons including Biological Components: Anthrax, Botulinum Toxins, Brucellosis, Cholera *Clostridium Perfringens* Toxins, Congo-Crimean Hemorrhagic Fever, Ebola Haemorrhagic Fever, Melioidosis*, Plague, Q Fever, Ricin, Rift Valley Fever, Saxitoxin, Smallpox, Staphylococcal Enterotoxin B, Trichothecene Mycotoxins, Tularemia, Venezuelan Equine Encephalitis, etc.

The apparatus described above can be used to apply Raman back scatter to detect various chemical components used as weapons or to create weapons including chemical components: Blistering Agents (sulphur mustards, nitrogen mustards, phosgene oxime, lewsite, phenyldichloroarsine, ethyldichloroarsine), Blood Agents (hydrogen cyanide, cyanogens halides, arsine), Choking Agents (phosgene, diphosgene), Nerve Agents ((G-Agents (tabun, sarin, soman, cyclohexyl methylphosphonofluridate), (V-Agents(vx)), Psychotomimetic Agents (3-quinuclidinylbenzilate, phencyclidine, LSD and the alike), etc.

The Raman spectrum, polarization and other characteristics for each of these composite materials are obtained either from the literature or by testing a sample of each material in vitro and storing the respective characteristics in a library.

Numerous other modifications may be made to the invention without departing from its scope as defined in the appended claims.

I claim:

1. An apparatus for testing targets for chemical weapon or biological weapon components comprising:

a laser beam source generating a laser beam, wherein said laser source generates two coincident laser beams;

a laser deflection system directing at least one of said two coincident laser beam at the target;

a collector receiving a portion of said laser beam scattered by said target; and an analyzer receiving said portion and generating an output indicative of the composition of compositions on the target.

2. The apparatus of claim 1 wherein said collector collects Raman back scatter.

3. The apparatus of claim 1 wherein said laser source generates said laser beam near the infrared region.

4. An apparatus for testing targets for chemical weapon or biological weapon components comprising:

a laser beam source generating a laser beam;

a laser deflection system directing said laser beam at the target;

a collector receiving a portion of said laser beam scattered by said target; and an analyzer receiving said portion and generating an output indicative of the composition of compositions on the target, wherein said laser beam source generates said laser beam with photons arranged in entangled pairs.

5. The apparatus of claim 4 wherein said laser source generates two coincident laser beams.

6. The apparatus of claim 4 wherein said source splits the laser portion into first and second beams, said first and second beams consisting of the respective photons of entangled pairs, with the first beam being directed toward the target and the second beam is analyzed to determine characteristics of said first beam after the first beam is scattered.

7. An apparatus for performing chemical composition analysis comprising: a laser beam source generating a first laser beam and a second laser beam, said laser beams consisting of respective first and second photons, each first photon being entangled a respective second photon;
- a laser deflection system directing said first laser beam at a target; and
- an analyzer receiving said second laser beam and generating an output indicative of the composition of compounds on the target.

8. The apparatus of claim 7 wherein said analyzer does not receive said first beam.

9. The apparatus of claim 7 wherein said analyzer includes a first analyzer portion receiving a portion of said first laser beam and a second analyzer receiving at least a portion of said laser beam, said analyzer portions analyzing said laser beams to generate a spectrum associated with the composition.

10. The apparatus of claim 9 wherein said analyzer portions generate Raman spectrums.

11. The apparatus of claim 7 wherein said analyzer also receives photons scattered from said first beam and generates a result dependent on said first and second beams.

12. A method of analyzing the composition of materials associated with a target, comprising:

generating a stream of photons;

directing said stream of photons at the target;

collecting photons scattered from said target; and generating a signal from said scattered photons indicative of said composition, wherein said step of generating said stream of photons includes generating a plurality of coincident photon beams.

13. The method of claim 12 wherein said scattered photons are indicative of Raman back scatter.

14. The method of claim 12 wherein said coincident photon beams are generated using Spontaneous Parametric Down Conversion.

15. The method of claim 12 wherein said coincident photon beams include pairs of entangled photons.

16. The method of claim 12 further comprising generating a first laser beam and a second laser beam, each said laser beam consisting of respective first and second photons, said first and second photons being entangled with each other to form pairs of entangled photons.

17. The method of claim 12 wherein the has a wavelength near infrared.

* * * * *